United States Patent
Suckewer et al.

(10) Patent No.: US 8,596,281 B2
(45) Date of Patent: Dec. 3, 2013

(54) DEVICES, METHODS AND COMPOSITIONS FOR PRESBYOPIA CORRECTION USING ULTRASHORT PULSE LASER

(76) Inventors: Szymon Suckewer, Princeton, NJ (US); Alexander Smits, Princeton, NJ (US); Peter Hersh, Far Hills, NJ (US); Richard Register, Princeton Junction, NJ (US); Gary Kunkel, Minneapolis, MN (US); Anatoli Morozov, Highstown, NJ (US)

( * ) Notice: Subject to any disclaimer, the term of this patent is extended or adjusted under 35 U.S.C. 154(b) by 1200 days.

(21) Appl. No.: 12/087,507

(22) PCT Filed: Mar. 5, 2007

(86) PCT No.: PCT/US2007/005648
§ 371 (c)(1),
(2), (4) Date: Apr. 30, 2009

(87) PCT Pub. No.: WO2007/103349
PCT Pub. Date: Sep. 13, 2007

(65) Prior Publication Data
US 2010/0076417 A1    Mar. 25, 2010

Related U.S. Application Data

(60) Provisional application No. 60/779,861, filed on Mar. 7, 2006.

(51) Int. Cl.
*A61F 9/008* (2006.01)

(52) U.S. Cl.
USPC .............................................. 128/898; 606/5

(58) Field of Classification Search
USPC ............................................... 606/5; 128/898
See application file for complete search history.

(56) References Cited

U.S. PATENT DOCUMENTS

2006/0083732 A1*  4/2006  Gwon ........................ 424/94.61

* cited by examiner

*Primary Examiner* — Shawquia Young
(74) *Attorney, Agent, or Firm* — Roy Rosser

(57) ABSTRACT

The invention relates to devices, compositions and methods used to improve vision and/or to treat an eye lens disease or condition. In some embodiments, the invention relates to altering or removing eye lens material for the treatment of presbyopia. In additional embodiments, the invention relates to placing compositions in a lens of an eye to improve elasticity of the lens both therapeutically by improving elasticity and/or improving refractive properties and/or prophylactically by preventing renewed stiffening and/or renewed deterioration of the lens refractive properties. In further embodiments, the invention relates to devices and methods of obtaining and analyzing data for use in altering the lens to optimize its elasticity and/or refractive properties.

8 Claims, 10 Drawing Sheets

DEVICES, METHODS AND COMPOSITIONS FOR PRESBYOPIA CORRECTION USING ULTRASHORT PULSE LASER

This application claims the benefit of U.S. Provisional Application No. 60/779,861, filed Mar. 7, 2006.

FIELD OF INVENTION

The invention relates to devices, compositions and methods used to improve vision and/or to treat an eye lens disease or condition. In some embodiments, the invention relates to altering or removing eye lens material for the treatment of presbyopia. In additional embodiments, the invention relates to placing compositions in a lens of an eye to improve elasticity of the lens both therapeutically by improving elasticity and/or improving refractive properties and/or prophylactically by preventing renewed stiffening and/or renewed deterioration of the lens refractive properties. In further embodiments, the invention relates to devices and methods of obtaining and analyzing data for use in altering the lens to optimize its elasticity and/or refractive properties.

BACKGROUND OF THE INVENTION

The eye focuses light on the retina by refracting incoming light as it passes through the cornea and by adjustably refracting the light through the eye lens by action of ciliary bodies. When the eye shifts from viewing a near object to viewing an object at a distance, the ciliary muscle within the ciliary body relaxes. The ciliary processes pull on the suspensory ligaments (zonules), which in turn pull on the lens capsule around its equator. This causes the entire lens to flatten or to become less convex, whereupon the focal point of light-rays emanating from the object migrates away from the lens toward the retina. Conversely, when the ciliary muscle works or contracts, tension is released on the zonules, and subsequently on the lens capsule, causing both lens surfaces to become more convex. The focal point migrates from behind the retina toward the lens and the eye is able to focus on near objects. Presbyopia is a condition in which the lens of the eye loses its ability to focus. The lens continually grows throughout life, laying new cells over the old cells resulting in a stiffer and thicker lens. The lens gradually loses its accommodation ability as the individual ages. There is no proven prevention for presbyopia. Thus, there is a need to develop methods that treat presbyopia or reverse the effects of presbyopia and improve vision.

SUMMARY OF INVENTION

The invention relates to devices, compositions and methods used to improve vision and/or to treat an eye lens disease or condition. In some embodiments, the invention relates to altering or removing eye lens material for the treatment or prevention of presbyopia. In additional embodiments, the invention relates to placing compositions in a lens of an eye to improve elasticity of the lens both therapeutically by improving elasticity and/or improving refractive properties and/or prophylactically by preventing renewed stiffening and/or renewed deterioration of the lens refractive properties. In further embodiments, the invention relates to devices and methods of obtaining and analyzing data for use in altering the lens to optimize its elasticity and/or refractive properties.

In some embodiments, the invention relates to a method of treating a subject having impaired vision comprising: A) providing: i) a subject diagnosed with, at risk for, or suspected of having presbyopia comprising an eye with an eye lens, and ii) a device comprising: a) a laser beam and b) a housing configured to support an eye of a subject in a fixed position; B) photoablating at least a portion of said eye lens with said device providing photoablated lens tissue; and C) removing at least a portion of said photoablated lens tissue so as to provide a removed lens tissue area. In further embodiments, said subject is a human over 50 years of age. In further embodiments, said laser beam comprises ultrashort pulse beams.

In some embodiments, the invention relates to a device comprising: a) a first laser beam, b) a second laser beam, and c) a housing configured to support an eye of a subject in a fixed position wherein said first laser beam is configured such that said beam is directed from an exterior of said eye to a eye lens tissue of said eye and wherein said second laser beam is configure to intersect said first beam in an interior of said eye lens tissue. In further embodiments, said first laser beam is an ultrashort pulse beam.

In some embodiments, the invention relates to a device comprising: a) a laser beam; b) a first light focusing object and a second light focusing object wherein said second light focusing object is configured to focus said laser beam; c) a first platform comprising a first motor configured to adjust a position of said first light focusing object d) a housing configured to fix a position of an eye of a subject wherein said first platform is secured to said housing; e) a second platform comprising a second motor configured to adjust a position of said second light focusing object; f) a third motor attached to said second platform wherein said motor is configured to adjust said second platform around said housing; and g) a microscope configured to view said eye of said subject through the inside of said housing. In further embodiments, the method further comprises a computer configured to control said microscope, said laser beam, and said positions of said first, said second, and said third motors. In further embodiments, said housing is cylindrical. In further embodiments, said third motor adjusts by rotating around said cylindrical housing. In further embodiments, said first light focusing object is a mirror. In further embodiments, said second light focusing object is a mirror.

In some embodiments, the invention relates to a method comprising: a) providing: i) a subject comprising an eye comprising eye lens tissue, ii) a device configured to photoablate eye lens tissue and iii) a polymeric solution; b) photoablating at least a portion of said eye tissue with said device providing photoablated lens tissue; c) removing at least a portion of said photoablated lens tissue so as to provide a removed lens tissue area; and d) adding said polymeric solution into said removed lens tissue area under conditions such that a polymer gels. In further embodiments, said gelled polymer has refractive index matching the refractive index of surrounding lens tissue. In further embodiments, said photoablated material is removed by a syringe. In further embodiments, said polymer solution is added by a syringe.

In further embodiments, the invention relates to a device comprising: a) a first laser beam, b) a second laser beam, and c) a housing configured to support an eye of a subject in a fixed position, wherein said first laser beam is configured such that said beam is directed from an exterior of said eye to a eye lens tissue of said eye and wherein said second laser beam is configured to intersect said first beam in an interior of said eye lens tissue. In further embodiments, said first laser and second laser beams are ultrashort pulse beams.

In further embodiments, the invention relates to a method comprising: a) providing: i) a subject comprising an eye lens, ii) a first ultrashort pulse laser beam, and iii) a second laser beam; b) directing said first laser beam from an exterior surface of the eye to an exterior surface of the eye lens; and c) directing said second laser beam to intersect said first beam under conditions such that said laser beams photoablates at least a portion of said eye lens tissue. In further embodiments, said first ultrashort pulse laser beam is between 100 femtoseconds and 1 picosecond. In further embodiments, said second laser is an ultrashort pulse laser beam. In further embodiments, the method further comprises the step of removing at least a portion of said photoablated tissue. In further embodiments, said removed tissue is greater than 5% of the eye lens by volume. In further embodiments, the method further comprises adding a polymeric solution to said eye lens. In further embodiments, said polymeric solution comprises a compound with a thiol group and a compound with an acrylate group.

In some embodiments, the invention relates to a method of removing eye lens tissue comprising: a) providing: i) a subject comprising an eye lens, ii) a first ultrashort pulse laser beam, and iii) a second laser beam; b) directing said first laser beam from an exterior surface of the eye to an exterior surface of the eye lens; and c) directing said second laser beam to intersect said first beam under conditions such that said laser beams photoablates said eye lens tissue. In further embodiments, said first ultrashort pulse laser beam is between 100 femtoseconds and 1 picosecond. In further embodiments, said second laser is an ultrashort pulse laser beam. In further embodiments, the method further comprises the step of removing said photablated tissue. In further embodiments, said removed tissue is greater than 5%, 10%, 20%, 30%, or 40% of the eye lens by volume. In further embodiments, the method further comprises the step of adding a polymeric solution to said eye lens.

In some embodiments, the invention relates to a system for making channels in the anterior tissues of the eye towards the eye lens comprising a) a subject having an eye with a lens; b) a beam of laser light, said beam being focusable into an anterior portion of said eye lens; c) a focusing apparatus capable of focusing said beam for a predetermined period of time, successively, at sites progressively deeper in said eye lens, under conditions such that a light transmissive channel forms in the material comprising said eye.

In some embodiments, the invention relates to a method of treating an eye disease, comprising a) providing a subject having an eye comprising a crystalline lens; b) directing a focusable beam of laser light along said light transmissive channel; c) focusing said beam to a focal point at a predetermined site within said lens; d) maintaining said focusing at said site for a period of time; and e) repeating step d) until subject's eye disease is improved. In some embodiments, the improvement may not be evident for days or weeks. In further embodiments, said eye disease is presbyopia.

In some embodiments, the invention relates to a method comprising: a) providing: i) an ultrashort pulse laser preferably less than 10 picosecond in duration, and ii) a subject comprising an eye lens comprising eye tissue, iii) a computer, and b) measuring dimensions of said eye lens; c) creating a computational model of said eye lens; d) computing an accommodation effect after a portion of said tissue is removed from a location in said computational model; e) changing to a second location, repeating step d) and f) photoablating said eye lens tissue with said ultrashort pulse laser providing photoablated lens tissue.

In some embodiments, the invention relates to a method comprising: a) providing: i) an ultrashort pulse laser, ii) a subject comprising an eye lens comprising eye lens tissue, and iii) a computer; b) measuring dimensions of said eye lens; c) creating a computational model of said eye lens; d) computing an amount of said eye lens tissue to be removed from a location in said eye lens creating an empty space such that upon collapsing said empty space a geometric shape of the eye lens assumes an new shape; and e) removing eye lens tissue from said eye lens according to the computed empty space. In further embodiments, the method further comprises the step of correlating said new shape to an idealized shape for improving accommodation.

In some embodiments, the invention relates to a method comprising: a) providing: i) an ultrashort pulse laser, ii) a subject comprising an eye lens comprising eye lens tissue, and iii) a computer; b) measuring dimensions of said eye lens; c) creating a computational model of said eye lens; d) computing an accommodation effect after a portion of said tissue is computationally (or virtually) removed from a location in said computational model; e) changing said location, to a second location wherein said tissue is computationally removed, and repeating step d) until said computational photablating is done at a location wherein said computed accommodation effect is maximized. In further embodiments, said computational model uses a parameter of a physical characteristic dependent on an age of said subject. In further embodiments, said accommodation effect is an amount by which the anterior and posterior lens surfaces flatten when pulling on zonules. In some embodiments, the method further comprises the step of computing an optimized volume of tissue to be removed from said lens.

In some embodiments the invention relates to a computer having software running thereon comprising a virtual lens comprising a) a lens capsule defined by a shape function, an elasticity function and a refractive index function; b) a lens subcapsular layer defined by a shape function, an elasticity function and a refractive index function; c) a lens cortex defined by a shape function, an elasticity function and a refractive index function; d) a lens nucleus defined by a shape function, an elasticity function and a refractive index function; and e) a zonule-ciliary muscle system defined by a forcing function.

In certain embodiments, the invention relates to modeling the lens with a finite element stress strain model to calculate its deformation under the pull of the ciliary bodies so that, in combination with the refractive properties of the lens one may then compute its accommodation: one may calculate the stress so that the resultant strain can be found. In additional embodiments, the invention relates to a method of mapping a stress point in a crystalline lens comprising a) providing a virtual lens; b) providing said crystalline lens; c) measuring an accommodative effect of said crystalline lens using existing optometric techniques; d) editing said virtual lens until said crystalline lens's accommodative effect substantially equals an accommodative effect of said virtual lens; and f) calculating a locus of said stress point in said edited virtual lens.

In some embodiments, the invention relates to a method of surgical intervention in a lens to correct for presbyopia. In preferred embodiments one uses a femtosecond laser to remove, by photoablation, prescribed portions of the eye lens, with the added possibility of replacing the removed parts of the lens with a polymer. Femtosecond lasers provide high intensity light at very low energy levels so that the ablation proceeds precisely, with negligible heating and collateral trauma.

In some embodiments, the invention relates to a method comprising the steps of (a) using an ultrashort pulse laser (pulse length preferably 100-300 fsec, but also as long as 1-10 psec and possibly up to 200 psec long) to photodisrupt (preferably photoablate or photointeract) lens tissue in the lens capsule of an eye, totally or partially removing the lens tissue; replacing the removed part by a polymer; (b) splitting an ultrashort laser pulse into N beams (preferably N=2 but N=1 and N>2 is also feasible) and cross-focusing them onto tissue in the lens of the eye for the purpose of its photodistruption (e.g. photoablation); (c) removing photodistrupted lens tissue in gaseous or liquid states by means of a small diameter hollow needle (syringe); and (d) replacing removed ablated tissue by injection of a polymer also using a small diameter hollow needle (syringe).

In further embodiments, a continuous wave laser in the visible range of the spectrum (for example, Helium-Neon, HeNe, or other CW laser) is split into N beams (where the value of N is the same as that given in claim 1) that follow the same paths as the ultrashort pulse laser beams, but not tightly cross-focused into the eye lens, to provide illumination of lens tissue, such that the procedure may be monitored using an optical microscope.

In further embodiments, a computer controlled positioning system position glass lenses for cross-focusing of the laser beams in three directions (along laser beam and orthogonal thereto) precisely on a given mass of eye lens tissue for purposes of photoablation, photointeraction, or imaging particular parts of the lens tissue.

In further embodiments, the tip of a hollow needle (syringe) of internal diameter less than about 200 µm (although larger diameters are not excluded) is inserted in the volume where tissue was photoablated followed by decreasing the pressure in such a syringe to aspire a portion or the full volume of photoablated lens tissue.

In further embodiments, the tip of a hollow needle (syringe) of internal diameter less than about 200 µm (although larger diameters are not excluded) is inserted in the lens capsule following partial of full lens removal and polymer material is pumped in the lens capsule, and the polymeric material closely matches the desired refractive index and material properties of eye lens tissue.

In additional embodiments, the invention relates to a method of photoablating a material by a) providing i) a transparent material ii) a first ultrashort pulse laser beam, and iii) a second laser beam; b) directing said first laser beam to an exterior surface of said transparent material; c) directing said second laser beam to intersect said first laser beam under conditions such that said laser beams photoablates the interior of said material. In further embodiments, said material is a tissue of a subject. In further embodiments, said tissue is eye lens tissue.

DETAILED DISCUSSION

Figure 1:
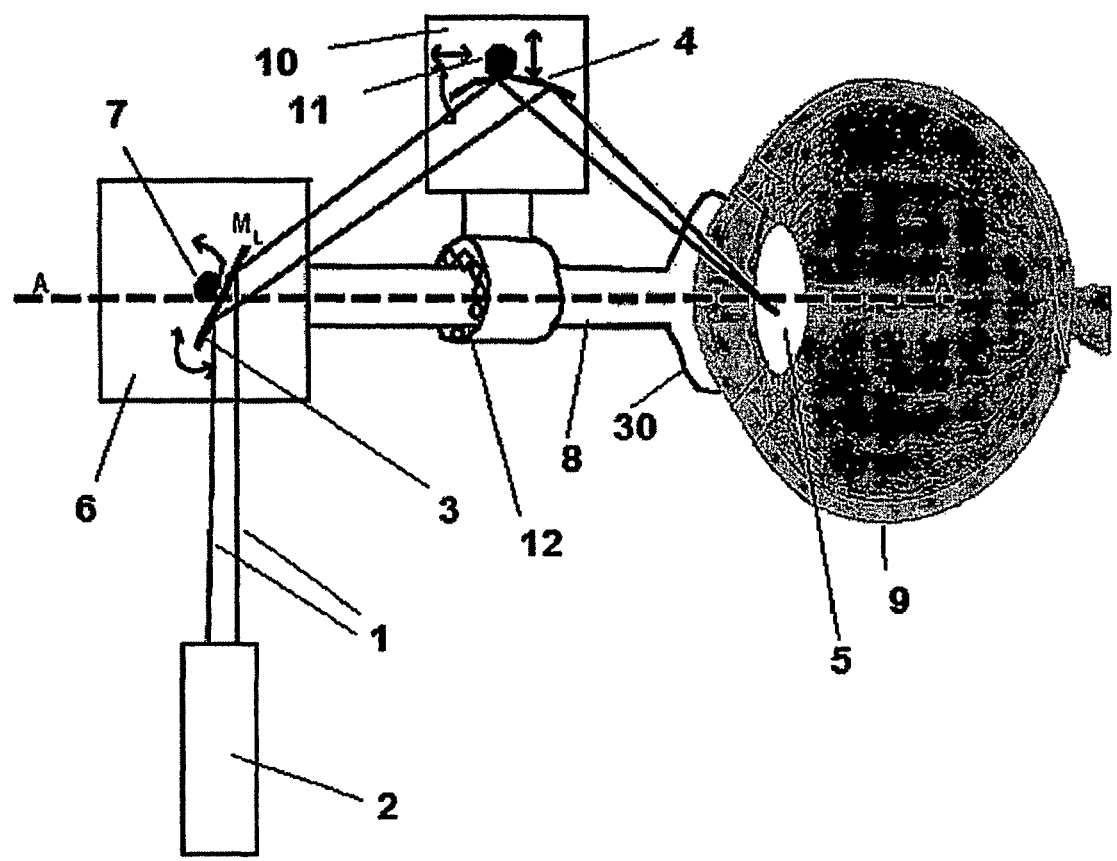
FIG. 1 shows schematically the setup for controlled ablation of lens material whereby a computer directs ultrashort pulsed laser beam(s) (preferably beams of femtosecond laser pulses although longer and shorter pulses are not excluded) into different parts of the lens by adjusting the laser beam positions using steering and focusing mirrors. This embodiment shows a device comprising: two laser beams (1); a laser (2); a first mirror which is a light focusing object (3) and a second mirror which is a light focusing object (4) wherein said second mirror is configured to intersect said two laser beams in the eye lens (5); a first platform (6) comprising a first motor (7) configured to adjust a position of said first mirror; a housing (8) configured to fix a position an eye (9) of a subject wherein said first platform is secured to said housing; a second platform (10) comprising a second motor (11) configured to adjust a position of said second mirror; a third motor (12) attached to said second platform wherein said motor is configured to adjust said second platform around said housing; and a microscope (13) configured to view said eye of said subject through the inside of said housing.

The invention relates to devices, compositions and methods used to improve vision and/or to treat an eye lens disease or condition. In some embodiments, the invention relates to altering or removing eye lens material for the treatment of presbyopia. In additional embodiments, the invention relates to placing compositions in a lens of an eye to improve elasticity of the lens both therapeutically by improving elasticity and/or improving refractive properties and/or prophylactically by preventing renewed stiffening and/or renewed deterioration of the lens refractive properties. In further embodiments, the invention relates to devices and methods of obtaining and analyzing data for use in altering the lens to optimize its elasticity and/or refractive properties.

Basic refractive errors of myopia, hyperopia, and astigmatism are currently correctable with excimer laser procedures such as LASIK. Although a number of procedures such as conductive keratoplasty, holmium laser thermokeratoplasty, and accommodative intraocular lenses can give functional near vision to older patients, no actual surgical correction of presbyopia is currently available. In some embodiments, the present invention relates to an apparatus and a procedure to surgically treat and reverse presbyopia via femtosecond laser surgery of the native crystalline lens.

As used herein an "ultrashort laser pulse" means about 1 femtosecond to 500 picoseconds long, where 1 psec=$10^{-12}$ sec, preferably between 100 femtoseconds to 200 picoseconds). In certain embodiments, the invention relates to using ultrashort laser pulses for restoring accommodation in the case of presbyopia, by removing tissue from the lens capsule of an eye, and refilling the eye capsule with polymeric material that has suitable material properties and refractive index properties.

As used herein the terms "photoablate" and "photoablation" and the like means the heating that follows the absorption of laser energy leads to the decomposition of a material.

The terms "eye lens" or "crystalline lens" mean the transparent structure in the eye that, along with the cornea, helps to refract light to focus on the retina. Eye lens tissue means any part of the crystalline lens. The lens capsule is a clear, membrane-like structure that is elastic, a quality that keeps it under constant tension. As a result, the lens naturally tends towards a rounder or more globular configuration, a shape it must assume for the eye to focus on objects at a near distance. Suspensory ligaments (i.e., zonules), which attach at one end to the lens capsule and at the other end to the ciliary processes of the circular ciliary body located around the inside of the eye, hold the lens in place.

"Accommodation" or the "accommodative process" means the adjustment in lens shape to focus at various distances. When the eye is viewing an object at a far distance (such that parallel rays of light are entering the eye), the ciliary muscle within the ciliary body relaxes. The ciliary processes pull on the zonules that in turn pull on the lens capsule at its equator. This causes the entire lens to flatten or to become less convex, enabling the lens to attempt to focus light from the far away object. Conversely, when the ciliary muscle works or contracts, tension is released on the zonules, and subsequently on the lens capsule, causing both lens surfaces to become more convex and the eye to be able to focus at near objects.

An "accommodation effect" means any change in elasticity or shape. Refractometers such as the Tomey QR-007 can be used to measure accommodation see Neveu and Stark, "The Virtual Lens," Presence 7: 370-381, 1998. The accommodation effect is measured in terms of diopters. A diopter is a unit of measurement of the optical power of a lens, which is equal to the reciprocal of the focal length measured in meters (that is, 1/meters). Accommodation (the maximum range between the smallest diopter and the largest diopter attained during focusing) is a function not only of the shape of the lens but also its material properties (for example, stiffness, refractive index, etc.). The lens continually grows throughout life, laying new cells over the old cells resulting in a stiffer lens. The lens tissue may also change its refractive properties such as it refractive index as the lens ages. The lens gradually loses its accommodation ability as the individual ages. The lens is made of transparent proteins called crystallins. The average concentration of lens proteins is about twice that of other intracellular proteins and is thought to play a structural role in the lens, with a lens refractive index (for visible wavelengths) varying from approximately 1.406 in the central layers down to 1.386 in less dense cortex of the lens.

An eye lens disease means any of a variety of diseases that cause impairment of vision due to a physical change in the normal operation of the lens including, but not limited to, nuclear sclerosis, presbyopia, and cataracts. A cataract is an opacification of the normally transparent crystalline lens that leads to blurred vision. Nuclear sclerosis is an increase in the density of the crystalline lens nucleus.

As used herein, "measuring dimensions" of an eye lens means any geometric or physical dimensions. The measurements can be done by a variety of methods including, but not limited to, laser ray-trace methods, ultrasound, and magnetic resonance imaging such as those described in Jones & Pope Magn Reson Imaging. 22(2):211-20 (2004), Rosales & Marcos, J Opt Soc Am A Opt Image Sci Vis. 23(3):509-20 (2006), and Vazquez et al., J Opt Soc Am A Opt Image Sci Vis. 23(10):2551-65 (2006).

In some embodiments, the invention relates to creating a computational model of an eye lens using a computer. A "computational model" or "mechanical model" means a set of data that represents the physical and/or geometric parameters of a real lens. Examples of creating computational models are described herein. In preferred embodiments, a portion of lens tissue is computationally removed from a location and the tendency of the lens to form a curve is determined, that is, relating to the overall elasticity of the lens. Alternatively, the ability of the anterior and posterior lens surfaces to flatten when pulling on the zonules is determined. It is also preferred to check this effect when different locations or different amounts of lens from different locations are varied in order to maximize the accommodation effect, given a refractive index distribution in the remaining lens material.

A laser beam means the light created from a laser. As used herein, a "laser" means a combination of parts and/or devices that amplify light by stimulated emission of radiation. The laser beam may be composed of continuous radiation (a "continuous wave" or "continuous waveform" or CW laser beam), or be composed of a train of pulses of radiation (a pulsed laser beam). A pulsed laser beam is described by a pulse length and a frequency of repetition of the pulse length. For example, a femtosecond pulsed laser may have a pulse length of 200 femtoseconds and a repetition rate of 1 kHz, although other pulse lengths and repetition rates are possible and cover wide ranges.

A light focusing object is any substance that transmits, bends or reflects a lightbeam or laser beam, such as, but not limited to, a mirror, crystal, prism, or lens.

As used herein, a "mirror" means a reflecting surface. Usually mirrors are made of plate glass, one side of which is coated with metal or some special preparation to serve as a reflecting surface. Highly polished metal and other materials serve also as mirrors. Three common types of mirror are the plane mirror, which has a flat, or plane, surface; the convex mirror; and the concave mirror. The concave type is one in which the midpoint or vertex of the reflecting surface is farther away from the object than are the edges. It is contemplated that, for some embodiments, a mirror may only reflect a narrow range of wavelengths. It is not intended that the mirror must reflect all light. A dielectric mirror is a mirror, made of a substrate, e.g., glass or some other optical material, on which one or more thin layers of dielectric material are deposited, to form an optical coating. By careful choice of the type and thickness of the dielectric layers, the range of wavelengths and amount of light reflected from the mirror can be specified.

The term "refractive index matching the refractive index of surrounding lens tissue" in relation to a polymeric material to be placed inside of a lens means that the refractive index is the same when the polymer hardens to the tenths place with a deviation of a tenth that is approximately 1.4±0.1 for most lens tissue. A "refractive index" is an inherent physically measurable property of a material designated by a number that is the factor by which the phase velocity of electromagnetic radiation is slowed in that material, relative to its velocity in a vacuum. Since the refractive index of a material varies with the frequency (and thus wavelength) of light, sometimes one will specify the corresponding vacuum wavelength at which the refractive index is measured. If not otherwise specified, the refractive index as provided herein is the refractive index at the Fraunhofer "D" line, the center of the yellow doublet sodium emission at 589.29 nm wavelength. A refractometer measures the extent to which light is bent (i.e. refracted) when it moves from air into a sample and is typically used to determine the index of refraction of a sample. In general, light changes speed as it crosses a boundary from one medium into another its direction of travel also changes, i.e., it is refracted. The relationship between light's speed in the two mediums, the angles of incidence and refraction and the refractive indexes of the two mediums is known. Thus, it is not necessary to measure the speed of light in a sample in order to determine its index of refraction. Instead, by measuring the angle of refraction, and knowing the index of refraction of the layer that is in contact with the sample, it is possible to determine the refractive index of the sample. The refractive index of certain media may be different depending on the polarization and direction of propagation of the light through the medium. "Refractive index" as used herein refers to the refractive index in the direction in which a laser beam is propagating.

As used herein "motor" means a combination of parts, such as a machine or an engine, that produces or imparts motion. In preferred embodiments, the motor is an arrangement of coils and magnets that converts electric current into controllable mechanical motion. However, it is not intended to be limited to electric powered devices.

As used herein, a "platform" means a surface for holding or supporting a part stationary. It is not intended to be limited by the shape of the platform.

As used herein, a "housing" means an enclosing frame. It is not intended to be limited to an entirely enclosed frame or by the shape of the frame.

As used herein, a "syringe" means an instrument used to inject compositions into a desired area, such as in a bodily tissue, or draw them from it.

Guidance of Laser Beam for Photoablation

In practice, the applicants have found that a typical laser beam cannot traverse 5-7 mm of lens tissue without some tissue interaction. Although perhaps not enough to damage the tissue, such interactions tend to frustrate light focusing when focusing is called for in the lens tissue (i.e., the tissue is not truly transmissive to light, so the light scatters and is absorbed). In order to access the eye lens, a laser beams can produce a channel by simply evaporating or burning material in its way. When applied to eye tissue, this procedure can cause undesirable damage to the eye tissue, and this result may be avoided if the purpose of creating a channel is to enable the laser energy to reach the crystalline lens.

The applicants discovered that femtosecond-pulsed beams of an appropriate intensity form channels extending from the corneal surface down to the desired focus site but do not damage the tissue. In this sense, a "light-transmissive channel" is distinguished over permanently open channels "drilled" into the sclera (as in the treatment of glaucoma, for example) or into the lens as conduits for the passage of fluid.

In certain embodiments, the invention relates to creating a light-transmissive channel that has an increased propensity to transmit light without scattering. In order to crate a light-transmissive channel in the eye and eye lens tissues, it is preferred to use a laser having a high repetition rate and low energy pulses, such as an ultrashort pulse laser. The laser beam from an ultrashort pulse laser is focused on at or near the surface of the eye with sufficient intensity to generate plasma by means of multi-photon ionization. By moving the focusing lens, the light-focusing channel is generated deeper and deeper in the eye tissue without damaging the tissue.

Theoretical Mechanism

Helmholtz first advanced the traditional view of the accommodative mechanism. In this theory, ciliary body contracture causes slackening of the lens zonules with consequent passive steepening of the crystalline lens as a result of its native elasticity. The ciliary muscle moves anteriorly and axially away from the sclera and the lens equator moves away from the sclera during accommodation. Ciliary body relaxation tenses the zonules, pulling the lens equator towards the sclera, and flattening the lens curvature for distance vision. During accommodation, investigators have found that the anterior pole of the lens moves forward, the posterior pole to a lesser extent, and the equator of the lens and nucleus are reduced in diameter.

In the Schachar theory of presbyopia, ciliary contraction increases tension on equatorial zonules while relaxing anterior and posterior zonules. This then causes central steepening of the lens while the periphery flattens. In this theory, presbyopia is caused by increased equatorial lens diameter with age. Hence, Schachar has proposed the surgical correction of presbyopia by increasing, with scleral implants the equatorial diameter of the ciliary body. Coleman & Fish have proposed a catenary theory of accommodation. Although the mechanism of accommodation is different from Schachar's theory, the catenary theory also suggests that lens volume increases with age cause presbyopia.

The applicants do not intend that the invention be limited by any particular mechanism. However, it is believed that there are a number of possible causes of presbyopia. The eye lens changes shape with age. The eye lens may harden with age. The eye lens may change its refractive properties with age. Capsular elasticity may change with age. Another mechanism may have to do with the changing architecture of the zonule-lens attachments. The anterior zonular attachment shifts forward with increasing age. Because of the increasing eye lens thickness and anterior shift of the insertion, there is a decrease in zonular insertion angle with a resultant decrease in capacity of the zonules to release tension when the ciliary body contracts. Finally, decreased function of the ciliary body with age could account for presbyopia. Evidence suggests that presbyopia may be multifactorial, with nuclear sclerosis accounting for a large portion of accommodative loss.

Eye Lens Surgery

Given that volumetric and morphologic considerations exacerbate presbyopia, femtosecond eye lens surgery affords a methodology for altering the optical and mechanical properties of the lens to restore accommodation. In this procedure, femtosecond laser pulses are used to remove some part of the eye lens volume, typically to diminish equatorial and/or antero-posterior eye lens volume. A typical procedure removes disk of tissue near the eye lens equator centered on the polar axis. Since the active area of lens growth appears to be within 100 microns of the equator, laser tissue removal may be most beneficially directed to that region. In addition, decreasing the antero-posterior diameter of the eye lens using femtosecond laser pulses is done in some cases in order to potentiate the biomechanical effects of the eye's zonules.

Ultrashort pulse lasers (with a pulse duration preferably between about 100 to 300 femtosecond) may be used to remove human eye lens material by very precise photoablation and/or photointeraction. Ultrashort laser pulses make possible photoablation and photointeraction even when the pulse energy is very low since the intensity is high, and they do not create undesirable heating and the formation of shock waves. Focusing can be achieved in any part of the eye lens, and the exact focus can be controlled by choosing the position of external focusing lens for the ultrashort pulse laser. By focusing an ultrashort laser beam on specific tissue in the eye lens, the tissue can be photoablated or changed. The amount of photoablated tissue and time of photoablation or photointeraction depend on the energy per laser pulse and the laser repetition rate, which can be varied over a wide range.

Photoablated tissue in the gaseous or liquid state can be removed from the eye lens by means of very fine hollow needle (syringe) of a preferred diameter of 50 to 200 µm. This needle may be inserted in the patient's eye lens in the location where the process of photoablation takes place and attached to a suction apparatus in order to remove the ablated material.

The same type of needle (syringe) can also be used to inject polymers with refractive coefficients closely matched to the material properties and refractive coefficient of the eye crystalline lens material to replace the photoablated tissue.

Photoablated tissue in the gaseous state can also be removed from the eye lens through the small diameter (20-100 µm) elongated channel (0.5-5 mm long) created by picosecond or femtosecond laser pulses.

With the development of laser procedures such as LASIK to help correct vision by reshaping the cornea of an eye, several other new laser eye procedures are being considered that concern photoablation of eye tissue. U.S. Pat. No. 4,538,608 hereby incorporated by reference, issued to L'Esperance, Jr. for "Method and Apparatus for Removing Cataractous Lens Tissue by Laser Radiation" discloses delivering laser energy into the anterior of the eye lens and scanning the laser beam in order to photoablate cataractous tissue. Bille (U.S. Pat. No. 5,246,435 "Method for Removing Cataractous Material" hereby incorporated by reference) discloses a procedure of laser energy delivery to separate lamellae in the stroma by focusing a laser beam between lamellae layers and photoablating tissue at the interface between these layers.

In some embodiments, the invention relates to methods where nanosecond (nsec) type laser beams are used (for example, 10-20 nsec excimer lasers, or 5-10 nsec Nd/YAG laser, where 1 nsec=$10^{-9}$ sec). With these nsec type pulse durations, each laser shot creates strong shock waves within the eye, and significant tissue healing is generated. Using lasers with shorter pulse durations may reduce heat. Therefore, compact ultrashort lasers (with pulse durations less than 10 psec, where 1 psec=$10^{-12}$ sec) were developed in the late 1980's. For example, T. Juhasz et al., U.S. Pat. No. 5,993,438 "Intrastormal photorefractive keratectomy" hereby incorporated by reference, T. Juhasz, U.S. Pat. No. 6,110,116 "Method for corneal laser surgery" hereby incorporated by reference, and T. Juhasz et al., U.S. Pat. No. 6,146,375 "Device and method for internal surface sclerostomy" hereby incorporated by reference disclose using ultrashort (picosecond and femtosecond) laser pulses for cutting the so called "flap" in LASIK surgery, for employing a photodisruption technique for reshaping the cornea, and for using transcleral photodisruption of tissue on the interior surface of the sclera.

Although, the applicants do not intend the invention to be limited by a particular mechanism, it is believed an explanation of photoablation phenomena is provided in G. Mourou et al. U.S. Pat. No. 5,656,186 "Method for controlling configuration of laser induced breakdown and ablation" hereby incorporated by reference, which discloses the relationship between laser fluence threshold for breakdown (and photoablation) in tissue and laser pulse duration. Fluence (symbol F) is the term used in photochemistry to specify the energy delivered in a given time interval (for instance by a laser pulse) and it is usually measured as the number of Joules deposited per square cm over a certain period of time (J/cm$^2$). Pulse duration is given the symbol τ, and is usually measured in psec. It is shown by Mourou et al. that, starting at a fluence level of F≈10 J/cm$^2$ at a pulse duration τ≈10 nanosecond (nsec), F decreases as $\tau^{1/2}$ over the range 10 nsec down to 10 picosecond, then decreases by a factor of two for pulse durations from 10 psec down to 1 psec, and then stays constant at F≈0.4 J/cm$^2$ down to 100 fsec. Therefore, for a pulse duration of ti 10 nsec, the typical energy (E) required to ablate a surface area of diameter D≈100 micrometer (µm) is E≈1 mJ, whereas with a pulse duration of τ≈100-200 fsec (for such short pulses a typical D 20 µm) the typical energy required is only E≈1.6 µJ. Hence, to photoablate tissue using fsec rather than nsec laser pulses the energy levels are more than 500 times smaller.

Certain embodiments of the invention take advantage of the above mentioned features of ultrashort (fsec and psec) laser pulses for partial or total removal of tissue from the lens capsule of an eye for the restoration of accommodation by using ultrashort laser pulses as a tool for precise photoablation. High precision and localization is achieved by cross-focusing N laser beams at one point in the tissue. The N beams can be obtained by passing one ultrashort laser beam through one or more laser beam splitters. The preferred number of beams is N=2, but N>2 or N=1 can also be used.

In other embodiments, the present invention is a method and an apparatus that uses ultrashort (fsec and psec) laser pulses for photointeraction of laser light with tissue in the crystalline lens. Photointeraction can lead to changes in the material properties of lens material, and can be used as an alternative treatment for presbyopia. High precision and localization is achieved by cross-focusing N laser beams at one point in the tissue, as in the application to the removal of tissue.

In other embodiments, the present invention is a method and an apparatus for the removal from the lens capsule of the gaseous or liquid products of tissue photoablation. When eye lens tissue changes its properties in a manner likely to promote accommodation due to the process of photointeraction, the amount and rate of removal of photoablation products should be controlled so as to keep the pressure in the lens capsule constant.

In other embodiments, the present invention is a method and an apparatus for the injection of polymer material into the lens capsule of an eye to replace the removed photoablated lens tissue.

In some embodiments, the invention relates to a method and apparatus for restoring accommodation of the human crystalline lens by changing the properties of tissue in the eye lens by photointeraction, or by photoablating tissue in the lens capsule of an eye, removing photoablated tissue, and replacing the removed photoablated tissue by polymer material.

In some embodiments, the invention relates to a method comprising splitting a laser beam into N beams (preferable N=2) cross-focused at the desired point in the lens capsule. For N=2 it is preferable that the entry angle of these two beams into the eye be smaller than 90° (although it is not limited to this angle). For N=1 (single beam), it is preferable for high precision that the laser focusing lens has a small f-number (for example, f/2 or f/3) in order to localize the focal spot precisely. For N=2 and N>2, the f-number can be larger (for example, f/6) and still provide very good localization. Photoablation of lens tissue then takes place, using ultrashort laser pulses (fsec or psec; preferably 100-300 fsec). The amount of tissue that is photoablated may be highly localized, or involve all of the lens material, or anywhere in between these two extremes. Photoablation leads to liquefaction or gasification of lens tissue. When photointeraction takes place, the lens tissue is not ablated but will experience changes in its mechanical and optical properties.

In some embodiments, the invention relates to a method comprising introducing a small diameter syringe (preferably 50 to 200 μm in diameter, although the diameter can be larger as well as smaller) into the region of photoablation to remove a part or all of the ablated tissue. It is preferred that the amount of gas or liquid is removed so as to restore normal pressure in the eye.

In some embodiments, the invention relates to a method comprising injecting a fluid through a small diameter syringe to replace the ablated tissue. This fluid, or "prepolymer", is subsequently reacted to form a gel, with a comparable index of refraction and tensile modulus to the undisturbed material in the crystalline lens. Gel formation within the lens capsule can proceed by physical gelation or via chemical reaction. The latter route includes, but is not limited to, polymerization and gelation through the reaction of complementary functional groups on components of the prepolymer mixture; chemically-initiated free-radical polymerization (through the addition of initiators well-known to those skilled in the art); or photopolymerization, via a low power laser or flash lamp focused on the injected polymer. It is also possible for the prepolymer to be partially polymerized prior to injection, giving it characteristics intermediate between those of a fluid and a solid.

The ultrashort laser beam energy may (but not necessarily uniquely) be in range 10-50 μJ (micro-joule) per pulse with a laser repetition rate of around 1-10 kHz (the repetition rate could be lower or higher than this number, and the particular repetition rate is not crucial for the procedure). For such ultrashort pulse lasers with pulse durations in the range 100 fsec up to 10 psec, the total procedure time for ablating a volume of 5-10 mm$^3$ of human eye lens tissue is expected to take several minutes for high repetition rates.

Mechanical Modeling of the Human Lens

Mechanical models of the lens are described in Kasprzak, Optal. Physiol. Opt. 20(1), 31-43 (2000) and Brown, Experimental Eye Research, 15, 441-459, (1972). However, these references do not describe the effects of surgical changes in lens geometry on the ability of the eye to focus. Finite elemental analysis of a mechanical model of the human lens, as disclosed herein, provides an excellent method of assessing the effectiveness of a proposed change in lens shape on restoring the ability to accommodate. The analysis may be used as a factor in determining the benefit of surgical attempts to change the lens response and shape in methods that attempt to address the symptoms of presbyopia.

DESCRIPTION OF THE PREFERRED EMBODIMENTS

Example 1

Ultrashort Pulse Laser

Figure 2:
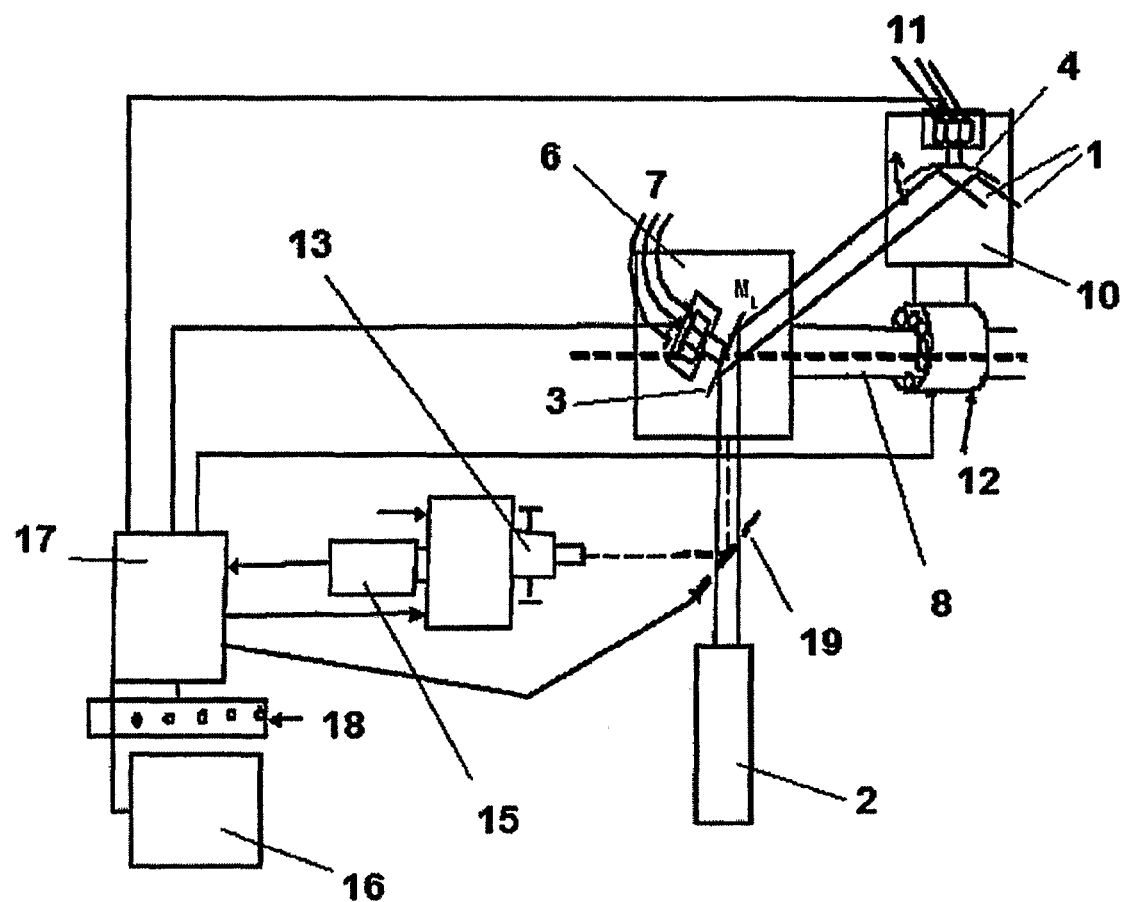
FIG. 2 shows schematically the control over the laser beam direction and its focal position in the eye lens using mirrors (3) and (4). The positions of mirrors (3) and (4) are controlled by micro-motors (7) and (11) (three on each platform), through a computer (17). The location of the laser beams (1) within the lens (5) and the process of ablation is monitored through a microscope (13) fitted with a CCD detector (15), connected to the computer (17) and monitor (16). Rotational motor (12) provides the ability to rotate platform (10) around the cylindrical housing (8) at a desired angle. The computer (17) is configured to change the position of mirrors (19), (3), and (4), control microscope (13) and analyze data from CCD detector (15).

One directs the laser beam (1) from "Fsec Laser" (see FIG. 1) by mirror (3) to spherical mirrors (4) which focus the laser beam into different locations within the eye lens. One places mirrors (3) and (4) on two separate platforms which are mechanically connected to the housing cylinder (8). One mounts on platform (6) on a mirror (3) that is rigidly connected to cylinder (8). The housing provides a stabilization mechanism (30) for the eye. One locates another mirror on platform (10) with mirror (4) that can rotate around cylinder (8) by means of the rotating mechanism (12). One synchronizes rotation of platform (10) with the angular movement of mirror (3) in such a way that the laser beam reflects from mirror (3) to always passes onto mirror (4). One sets the angle of mirror (3) by micro-motors, which are controlled and monitored by computer. The angle and position of mirror (4) on platform (10) are also set by micro-motors, which are controlled and monitored by the same computer. In this way, one can focus the "Fsec Laser" beam by mirror (4) into any part of the eye lens. FIG. 2 shows how one sets the laser beam direction and focus position in eye lens using mirrors (3) and (4). One monitors the position of the laser beam within the lens, and the process of ablation through a microscope outfitted with a CCD detector where the signal is directed to the computer and a monitor.

One may use a laser with pulses ranging from 100-300 fsec to 10 psec in duration, operating at a wavelength near 800 nm, at repetition rates 1 kHz or higher, and with preferable energy per pulse of 0.5 miliJoule or less. The wavelength of the pulse could be longer, but one prefers that the cornea and eye fluids are transparent at the chosen wavelength. For lens ablation, the wavelength of the laser is not of prime importance.

In order to abate and/or remove some particular portion of the eye lens material, for example, a "disc" 2 mm in diameter and 100 micrometers thick located 1 mm below the surface of lens (5) at its center, one focuses, via the mirror (4), the laser beam (1) initially on the central part of the lens aiming for a spot 1 mm below the surface. By the action of the laser beam, one creates a "channel" of a very small diameter (of order 100 micrometers in diameter) through which the laser beam passes to focus at the desired location, 1 mm below the surface of the lens, and begins ablating lens material. In order to ablate a disc of material, one rotates the platform (10) around housing cylinder (8) (axis of rotation: (14)). By changing the position of mirror (4) on the platform (10) and by changing its direction (angle), the laser beam can ablate a disc of material of a given diameter. One controls the thickness of such a disc by controlling the number of laser shots delivered to any given point within the disc. In this manner, the uniformity of the ablation throughout the disc can also be controlled. One monitors the ablation process in terms of location and uniformity using an optical microscope (13) through standard techniques such as those presently applied in laser eye surgery. As necessary, one can form additional channels in the lens to help remove gases that may form in the lens as the lens tissue is ablated.

Figure 3:
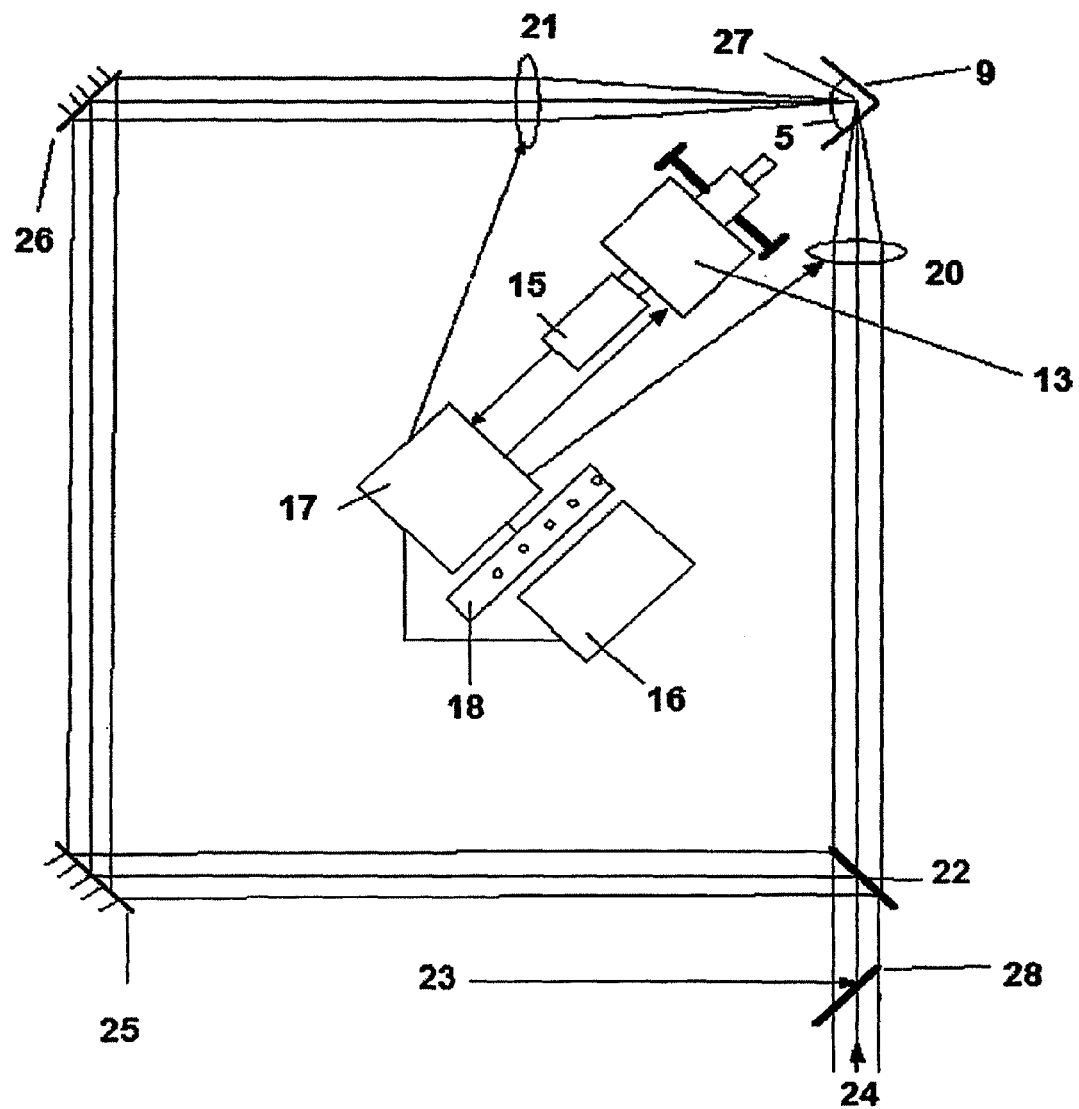
FIG. 3 is a schematic presentation of two ultrashort pulse laser beams (23) and (24) cross-focused at a point location (27) in the eye lens capsule (5) of the patient's eye (9), together with a microscope (13) for monitoring the interaction of the laser beams with eye lens tissue. Images from the microscope are recorded using a camera (CCD array) (15) connected to a computer (17) and monitor (16). The computer provides position control for the lenses (20) and (21) and microscope objective. In this embodiment the device comprises: a first laser beam (23) and a second laser beam (24); a laser beam splitter (22) configured to split said first and second laser beams; a first light focusing object (20) wherein said first light focusing object is configured to focus said first and said second laser beams in the lens of an eye; a second light focusing object (21) wherein said second light focusing object is configured to focus said first and said second laser beam in the lens of an eye and wherein said first and said second light focusing objects are configures to focus said first and second laser beams into the same location (27) in said eye wherein a microscope configured to view said eye at said focusing location and wherein said second laser beam can be viewed with said microscope.
Figure 4:
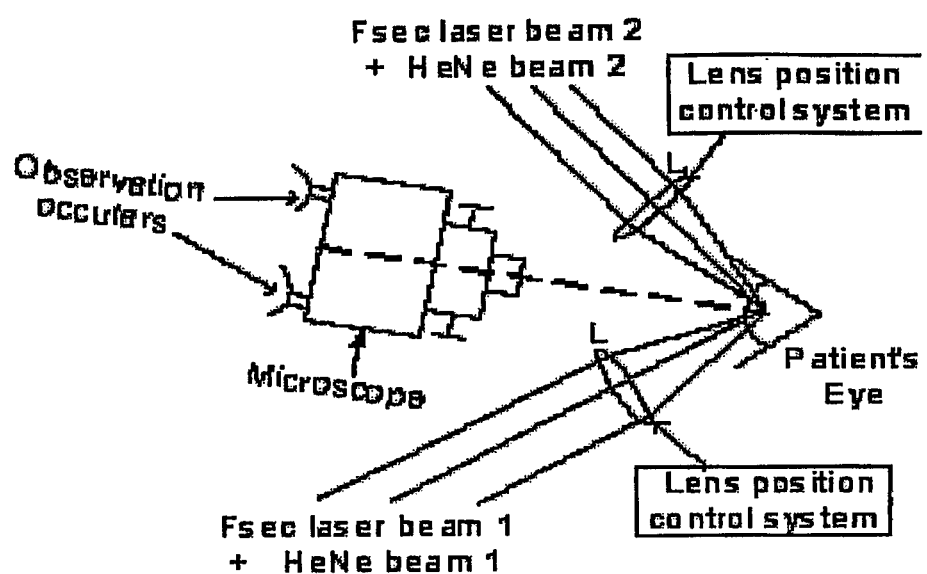
FIG. 4 is a schematic showing the arrangement of two ultrashort pulse laser beams, which are cross-focused in the patient's eye, showing how their interaction with eye lens tissue at the point of crossing of the beams is observed through an optical microscope. The continuous wave (CW) HeNe laser beams provide illumination of the tissue along the paths of both fsec beams and allow observation of the tissue after each laser pulse through the microscope.
Figure 5:
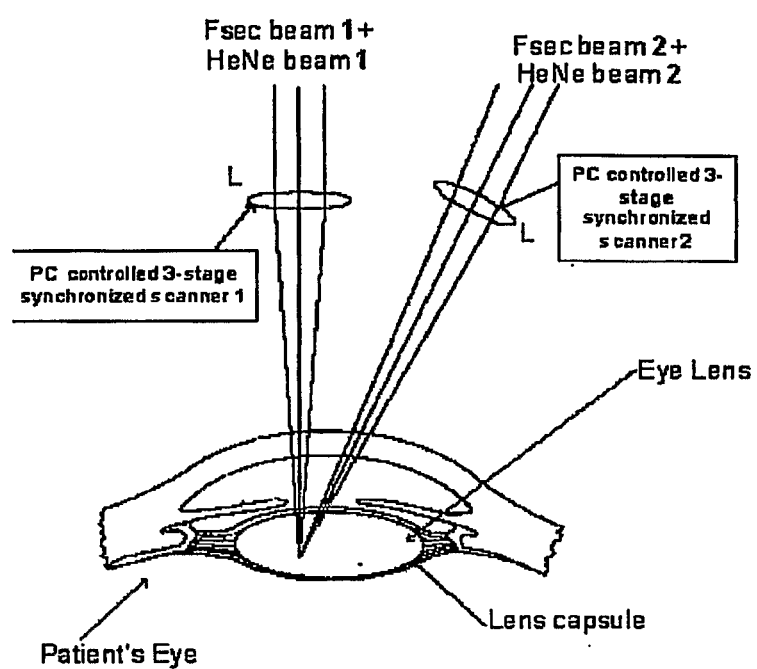
FIG. 5 illustrates a cross-section of a patient's eye shown in the plane of the laser beams indicating how the beams are focused at a point inside the eye lens capsule. The computer (PC) controls the lens L position to allow synchronized scanning through the eye lens volume.

The layout of another embodiment of the invention is presented in FIG. 3. The preferred embodiment in this case consists of N=2 ultrashort laser beams (N can also be 1 or greater than 2) that one focuses at a point inside the lens capsule of a patient's eye using lenses (20) and (21). For N=2, one splits the ultrashort laser beam into two approximately equal intensity beams by splitter (22). The preferred ultrashort laser beams are those of pulse duration $\tau$=100-300 femtoseconds (fsec), although $\tau\approx$1-10 picoseconds (psec) or less than 100 fsec may also be used. For N=2, the angle between the two focused beams is typically near 90° or less (the choice of angle may depend on the size and location of tissue to be ablated in the lens capsule and is not restricted to 90°. One may choose the location of the spot to be irradiated by ultrashort laser pulses by using a microscope and scattering HeNe (Helium-Neon) laser beams operating in the visible spectrum range at wavelength $\lambda$=632 nm, although any laser beam in the visible spectrum can be used instead. One places the HeNe laser beam (23) on the path of the fsec beam by mirror (28), which is transparent for ultrashort laser beams, where the ultrashort beam (24) preferably operates at a wavelength of $\lambda$=800 nm. One splits the HeNe beam (23) by splitter (28) into two beams, each of them following the same path of the ultrashort laser beams, but because they have a different wavelength the HeNe beams are not tightly focused by lenses (20) and (21) into the patient's eye (9). The crossing of HeNe laser beams in the eye (9) illuminates the lens material. One magnifies the image by the microscope (13) and observes the image on the monitor (16), providing a fast and simple method of choosing lens tissue to be photoablated or photointeracted by the ultrashort laser beams. One moves the focusing lenses (20) and (21) in the perpendicular (horizontal x-axis) and parallel (z-axis) direction as well as vertical (y-axis) relative to the plane of the beams using a three stage, remotely controlled, high precision position control system (micro-scanner) (see FIG. 4). The operator chooses the position of the crossing point by observing the microscope images on the monitor and giving instructions to the control system via the computer interface. One controls the depth of focus of the microscope either by the computer (FIG. 3) or manually by the operator (FIG. 4). For the microscope's detector, a CCD camera can be used (FIG. 3), or one observes directly the eye tissue by a person through the microscope (FIG. 4). FIG. 5 shows a cross section of an eye with two ultrashort beams (1 and 2) cross-focusing in the lens inside the lens capsule. Along the paths of the ultrashort beams, two CW beams of HeNe laser are also shown. By synchronously scanning both focusing lenses (20) and (21) along all three axes (x,y,z), one illuminates any given spot inside the lens capsule by the HeNe beams and photoablates by the ultrashort beams.

Figure 6:
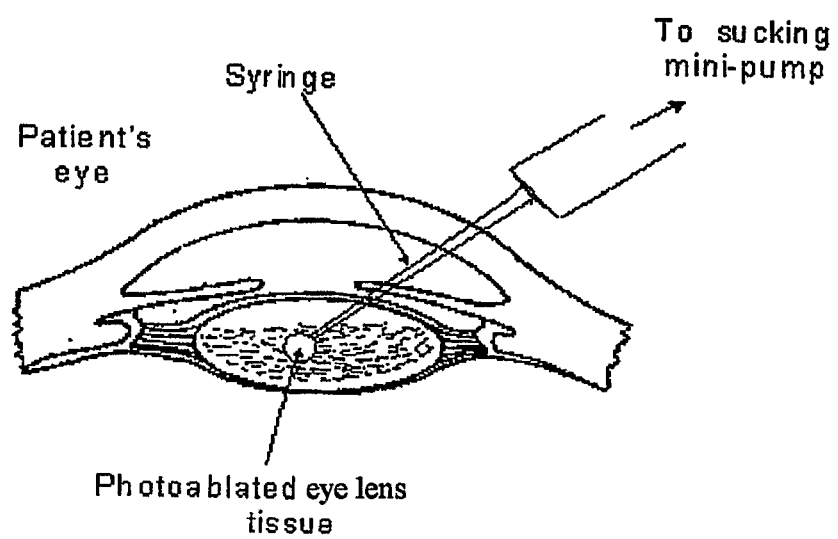
FIG. 6 illustrates a cross-section of a patient's eye indicating how the needle (syringe) is inserted into the photoablated volume of eye lens tissue to permit removal of the photoablated lens tissue.

One removes any portion of photoablated lens tissue, either in gaseous or liquid form, using a hollow needle (syringe) with a very small internal diameter (port) inserted into the eye lens and connects to a small evacuating pump (the "suction mini-pump" indicated in FIG. 6). One prefers the port to be smaller than that used in current cataract surgery procedures. In an even more preferred embodiment, the port is less than 200 $\mu$m in diameter (although greater or smaller sizes can also be used). One makes the syringe of transparent materials such as quartz or non-transparent metal materials (e.g. stainless steel) for better durability. Given a total volume of effluent comprising approximately 1 mm$^3$ (0.001 cubic centimeter or cc) one expects flow rates of the order of 0.0001 cc/sec if one assumes a removal/irrigation time of about 10 seconds. One may use multiple ports to ensure uniform and clean removal of effluent.

In some embodiments, two (or more) syringes may be used, where one or more syringe is used to evacuate ablated or other unwanted material from the lens capsule, and one or more syringes are used to flush (or "irrigate") the ablated material into the evacuating syringes by injecting water or other flushing liquid into the lens or the material contained in the lens capsule.

Figure 7:
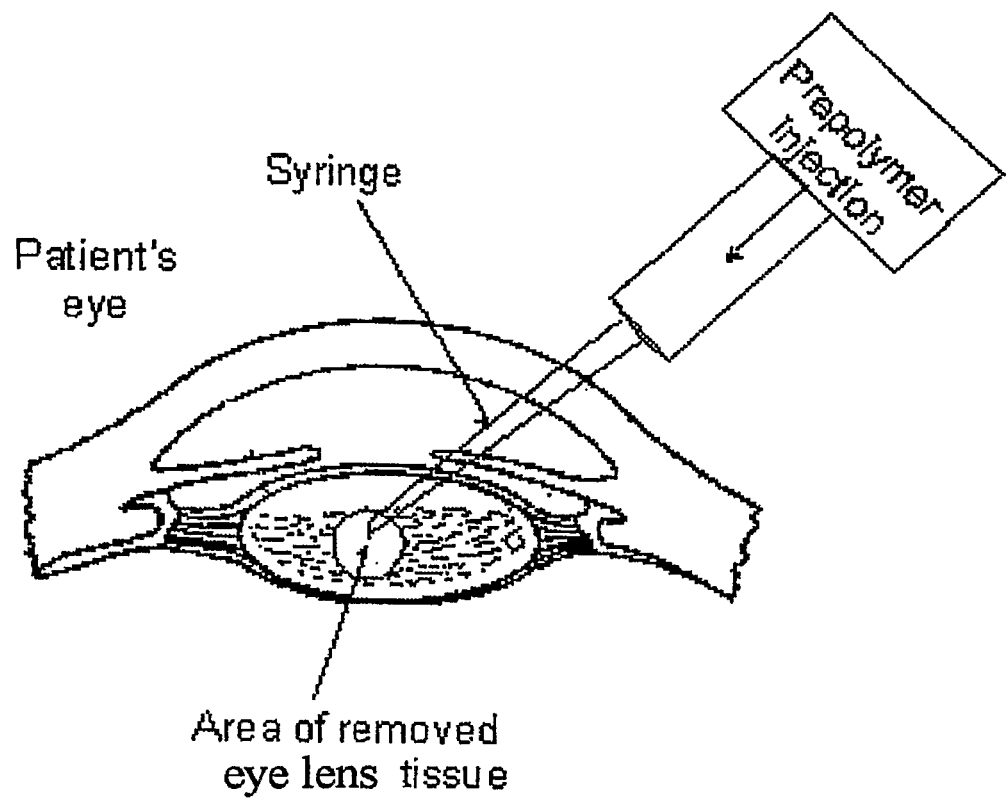
FIG. 7 illustrates a cross-section of a patient's eye indicating how the needle (syringe) is inserted into the photoablated volume of eye lens tissue to permit injection of polymer into lens capsule.

One uses a similar syringe or syringes for injecting prepolymer to replace the removed photoablated lens tissue. For injection purposes, one operates the mini-pump in reverse to push the prepolymer into the lens capsule of the eye, as can be seen schematically in FIG. 7. One places the tip of the needle in the lens capsule of the eye in a location where photoablated lens tissue was removed. The injected prepolymer should preferably be in a liquid state, but it can also be in a gel or a solid state. The prepolymer is preferably compatible with eye crystalline tissue in terms of material properties, index of refraction, transparency, stability and longevity (be able to maintain material properties, transparency and index of refraction for a large number of years), and preferably is benign in terms of its impact on human cells.

One photoablates an amount of material. If in a gaseous state, it is possible to avoid using a syringe to remove the material. However, one may create a small diameter (in range 20-100 $\mu$m) elongated channel (up to 5 mm long) by means of ultrashort laser pulses (pico- or femtosecond pulses) in the eye lens to connect the outside air to the point where ablation took place. If one creates such a channel, the photoablated material escapes from the eye without further intervention. Such small channels usually heal quickly (within minutes) without further intervention.

Example 2

Computer Program and Procedure

Figure 8:
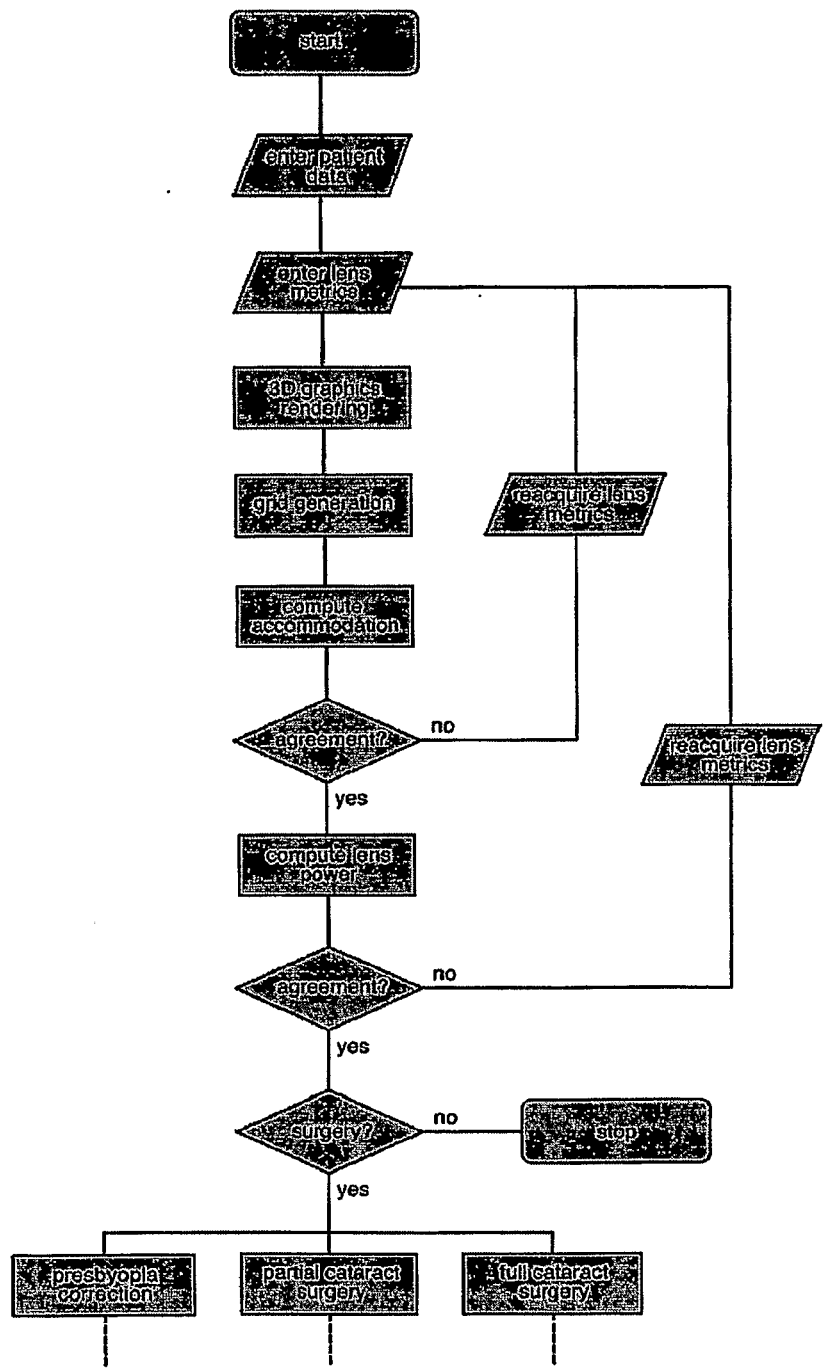
FIG. 8 illustrates a flow chart for lens surgery decision making.
Figure 9:
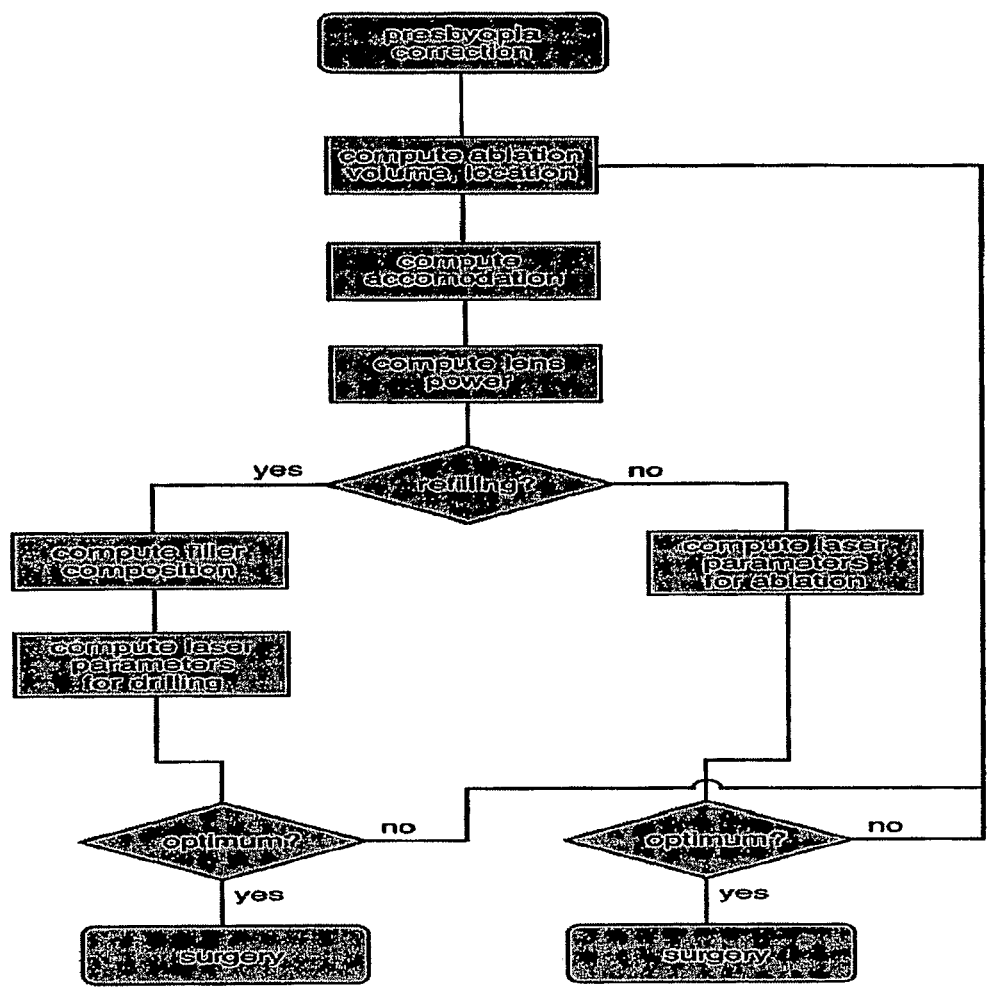
FIG. 9 illustrates a flow chart for the presbyopia correction procedure.
Figure 10:
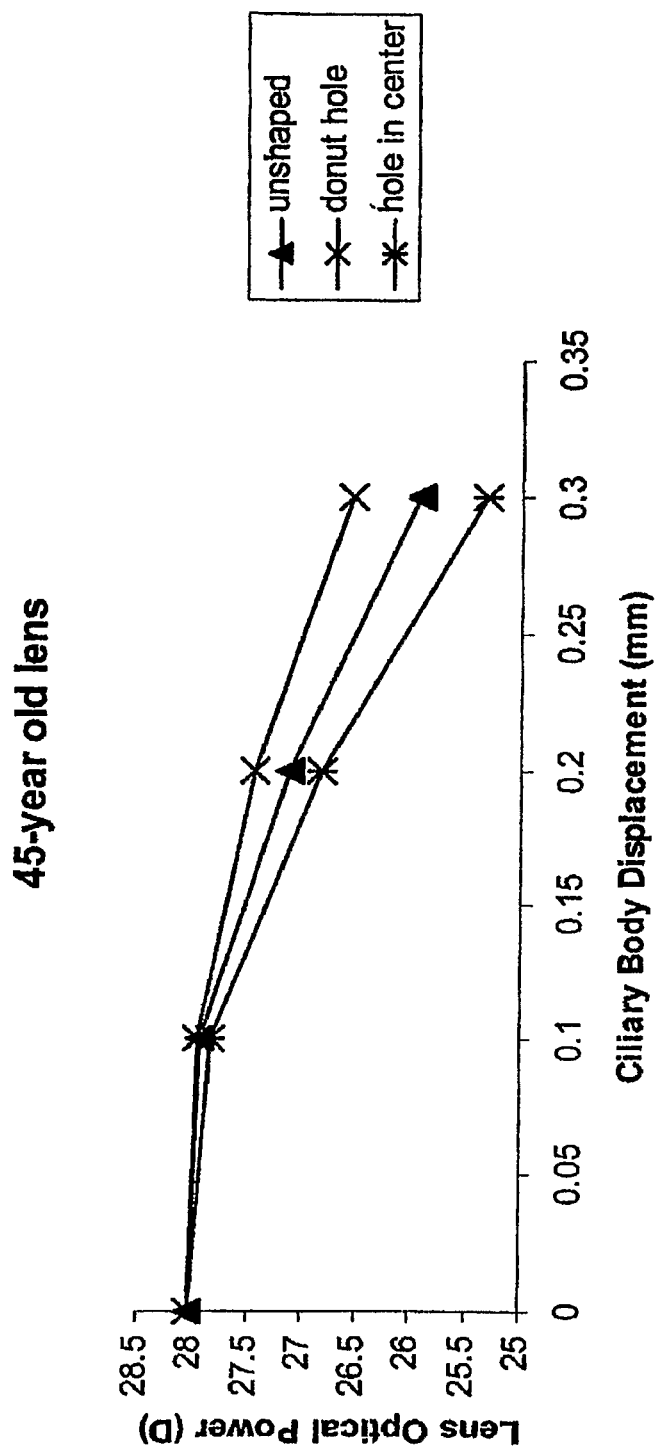
FIG. 10 shows data of calculations on the effect of removing lens material from a predetermined location.

FIG. 8 shows a flow chart of the procedure for laser surgery of the human eye lens using specifically-designed software. It ends in a decision tree, with four possibilities: presbyopia corrective surgery, partial cataract surgery, full cataract surgery, or no surgery. FIG. 9 shows the flow chart for presbyopia correction, the particular procedure of interest here.

In certain embodiments, the software executes a method comprising three steps. One enters patient-specific data on lens metrics (for example, size, shape, Young's modulus distribution, refractive index distribution, range of accommodation) and computes the optical and mechanical performance of the particular lens. In some embodiments, one may use a commercially available design tool (possibilities include, but are not confined to, AutoCAD, CATIA and ProEngineer) to model the geometry of the lens, its capsule and the ciliary muscle attachments. In further embodiments, one models information not available from the patient using population norms. One imports the geometry into a grid generation program (possibilities include, but are not confined to, GRIDGEN), and the grid is then exported to a finite-element program for computing stresses and strains under the action of the ciliary muscles (possibilities include, but are not confined to, ABAQUS). The muscle action changes the lens shape, and one compares the resulting lens shapes computed by the stress-strain analysis to the actual lens shapes measured in the patient. If the agreement is not satisfactory, one reacquires the lens metrics, and the computation is started afresh. If the agreement is satisfactory, one proceeds to the next stage, where one computes the optical power of each lens shape, using patient-specific values of the refractive index (where available, otherwise population norms may be used). The output consists of the variation of the optical power of the lens (usually expressed in diopters) as a function of the ciliary body displacement. This variation defines the accommodative range of the lens. One compares the output to the actual accommodation and actual lens power measured in the patient, and if the agreement is not satisfactory, one reacquires the lens metrics, and the computation is started afresh. If the agreement is satisfactory, one proceeds.

At this point one makes a decision regarding surgery. The surgeon uses the output to make one of four choices: presbyopia corrective surgery, partial cataract surgery, full cataract surgery, or no surgery. One bases the decision on the level of corrective surgery required, the presence or absence of cataracts or other lens defects, the general health of the patient, as well as other relevant medical input.

If one makes a decision to proceed with corrective surgery for presbyopia, one uses an optimization scheme to determine the minimum lens volume that needs to be removed from the lens and its location, and if refilling using polymeric materials as required. For example, one proposes a candidate volume. This candidate is a starting point for the optimization, and can be a pre-assigned size, shape and location based on previous experience. One considers multiple ablation volumes. One proceeds, as described above, computing the accommodation and the lens power over the range of patient ciliary body motion (using patient specific data where available, otherwise population norms may be used). For large ablation volumes, one considers refilling. The computations for refilling and not refilling may proceed in parallel. One makes a decision when an optimum solution is found. Under the refilling option, one computes the filler composition to match the refractive index and Young's modulus of the ablated material (as closely as possible), and the laser parameters (power per shot, number of shots, repetition rate, positioning and focusing of laser beam(s), shot pattern) for drilling access channels to deliver the refilling material. To determine the optimum surgical option, one computes a cost function on the basis of minimum ablation volume, most peripheral position of volume, maximum accommodative range, fewest delivery channels, and other additional constraints. The computation is then restarted using a small perturbation from the original volume choice, and the cost function is recomputed. One finds an optimal surgical strategy through this process. Under the no refilling option, one follows a similar optimization strategy, but the cost function will not contain reference to channel drilling for delivery.

The output from this software suite (when presbyopia correction is recommended) consists of specific instructions for the size, shape and location of the ablation volume(s), the details of the refilling material and associated delivery requirements (if refilling is recommended), the laser parameters recommended to achieve the specified ablation volume and channel drilling (if necessary). One uses the instructions on the laser parameters (power per shot, number of shots, repetition rate, positioning and focusing of laser beam(s), shot pattern) directly to program the laser output and the laser positioning system.

Example 3

Stress Distributions During Accommodation

One of the advantages of using ABAQUS instead of Pro-engineer for further analysis was to detail the stress distributions developed in the lens during the process of accommodation. Simulations showed that the greatest stresses occurred at the point of attachment of the zonules and the lens. The maximum in-plane stresses occur at the equatorial region of the lens. By various changes in geometry one can evaluate surgical impact on restoring accommodation. After introducing various incisions into the lens, the model can be stressed and the resulting optical power calculated.

In the first attempt to increase the amplitude of accommodation a small donut hole was make in the lens. This was done by creating a circular hole of a radius of 0.3 mm in the axisymmetric cross section of the lens. The hole was assumed to remain empty; however, the hole could be filled with water or other fluid with desired mechanical properties. The deformed lens shape seems to show that the donut hole reduces the amount by which the anterior and posterior lens surfaces flatten during accommodation, thus reducing the ability of the eye to focus. A spherical hole in the center, however, leads to an increased flattening of these surfaces.

By extracting the points defining the lens surface, the optical power of the altered lens can be computed analytically. The donut hole worsened the performance of the lens, and the spherical hole in the nucleus improved it. In preliminary studies, it was found that removal of material from the inside causes the lens to collapse inward, filling up the gap created.

Example 4

Modeling of Ablating and Refilling the Human Lens

Once one finds the optimal lens geometry for restoring accommodation by using the lens models described above, one uses computational fluid dynamics analysis to determine the best method of removing the emulsified lens material from the capsule. One develops a rendering of a lens using GAMBIT, a computational fluid dynamics preprocessing program, using the same properties as the ABAQUS meshes. One uses FLUENT, a computational fluid dynamics package, to study the fluid flow in the eye during this process. Once one determines the exact sections of the lens to be removed, one uses FLUENT to track particles in the lens to determine the percentage of effluent material that can be removed in a given period of time. This procedure can also be used to study the effects of one or more removal ports, and also the effectiveness of one or more flushing ports (irrigation) where liquids are introduced to flush out the non-gaseous debris resulting from the ablation.

Example 5

Polymer Augmentation Procedure

In those cases where the lens needs to be augmented, or a portion of the lens reconstituted, one adds a polymeric hydrogel material to the lens. One delivers the polymer to the lens as a liquid formulation of moderate viscosity, which may be injected to the lens via one or more syringe, or capillary, or other means known in the art. Once inside the lens, the liquid gels to a solid material that possesses satisfactory mechanical and optical properties to behave as an accommodative human lens. The material is preferably biostable and not subject to degradation over extended periods.

The fluid is preferably an aqueous solution of one or more biocompatible polymer elements, such as poly(ethylene oxide) or poly(ethylene glycol), poly(hydroxethylmethacrylate), poly(hydroxyethylene acrylate), or other polymers known or found to be biocompatible. One may add other species to the fluid solution as needed to create or promote the gelling process, or to modify the optical or mechanical properties of the hydrogel.

The gelation process may be by any of several methods known in the art. The gelation could be physical, induced by changes in temperature, pH, or ion concentration. More preferably, the gelation is chemical, resulting from chemical reactions which form covalent bonds and crosslinks between polymer chains and/or other molecules in the fluid mixture. These reactions may be triggered by any of several methods known in the art, such as photopolymerization initiated by visible or ultraviolet light, or free-radical polymerization initiated by free-radical generators such as peroxides, azo compounds, or redox couples. Most preferably, the reaction will process at physiological temperature, pH, and ionic strength, without the addition of separate initiators or irradiation with visible light, by mixing two or more complementary reactants to form the fluid mixture immediately prior to injection, and which produces no byproducts. An example of a suitable reaction is the Michael addition of compounds comprising multiple thiols to acrylates or acrylamides including polyethylene terminated acrylates to form crosslinked compositions.

The invention claimed is:

1. A method comprising:
a) providing:
   i) a subject comprising an eye comprising eye lens tissue;
   ii) a device configured to photoablate eye lens tissue; and
   iii) a polymeric solution;
b) photoablating at least a portion of said eye tissue with said device providing photoablated lens tissue;
c) removing at least a portion of said photoablated lens tissue so as to provide a removed lens tissue area; and
d) adding said polymeric solution into said removed lens tissue area under conditions such that a polymer gels.

2. The method of claim 1, wherein said device comprises:
a) two laser beams;
b) a first light focusing object and a second light focusing object wherein said second light focusing object is configured to intersect said two laser beams;
c) a first platform comprising a first motor configured to adjust a position of said first light focusing object;
d) a housing configured to fix a position of said eye, wherein said first platform is secured to said housing;
e) a second platform comprising a second motor configured to adjust a position of said second light focusing object;
f) a third motor attached to said second platform wherein said motor is configured to adjust said second platform around said housing;
g) a microscope configured to view said eye of said subject through the inside of said housing;
h) a computer configured to control said microscope, said two laser beams; and said positions of said first, said second, and said third motors.

3. The method of claim 1, wherein said gelled polymer has refractive index matching the refractive index of surrounding lens tissue.

4. The method of claim 1, wherein said photoablated material is removed by a syringe.

5. The method of claim 1, wherein said polymer solution is added by a syringe.

6. The method of claim 2 wherein at least one of said two laser beams is an ultrashort pulse laser beam.

7. The method of claim 6 wherein said ultrashort pulse laser beam pulse is less than 10 picoseconds in temporal duration.

8. The method of claim 6 wherein said ultrashort pulse laser beam pulse is between 100-300 femtoseconds in temporal duration.

* * * * *